United States Patent
Fiorella

(10) Patent No.: US 8,460,301 B2
(45) Date of Patent: Jun. 11, 2013

(54) SYSTEMS AND METHODS FOR MINIMALLY INVASIVE STABILIZATION OF BONY STRUCTURES

(75) Inventor: David L. Fiorella, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 621 days.

(21) Appl. No.: 12/694,790

(22) Filed: Jan. 27, 2010

(65) Prior Publication Data

US 2011/0184464 A1    Jul. 28, 2011

(51) Int. Cl.
*A61B 17/70* (2006.01)

(52) U.S. Cl.
USPC ...................................... 606/86 A

(58) Field of Classification Search
USPC ...................................... 606/86 A
See application file for complete search history.

(56) References Cited

U.S. PATENT DOCUMENTS

| | | | |
|---|---|---|---|
| 6,530,929 B1 | 3/2003 | Justis et al. | |
| 7,188,626 B2 | 3/2007 | Foley et al. | |
| 7,476,240 B2 | 1/2009 | Raymond et al. | |
| 7,497,869 B2 | 3/2009 | Justis | |
| 7,520,879 B2 | 4/2009 | Justis et al. | |
| 7,527,638 B2 | 5/2009 | Anderson et al. | |
| 7,993,344 B2 * | 8/2011 | Pond et al. | 606/86 A |
| 8,152,714 B2 * | 4/2012 | Garcia-Bengochea et al. | 600/114 |
| 8,172,855 B2 * | 5/2012 | Abdou | 606/99 |
| 2004/0039384 A1 * | 2/2004 | Boehm et al. | 606/61 |
| 2005/0171540 A1 | 8/2005 | Lim et al. | |
| 2006/0111713 A1 | 5/2006 | Jackson | |
| 2007/0049931 A1 * | 3/2007 | Justis et al. | 606/61 |
| 2007/0078460 A1 | 4/2007 | Frigg et al. | |
| 2007/0233079 A1 | 10/2007 | Fallin et al. | |
| 2007/0299443 A1 * | 12/2007 | DiPoto et al. | 606/61 |
| 2008/0077138 A1 * | 3/2008 | Cohen et al. | 606/61 |
| 2008/0312703 A1 * | 12/2008 | Hestad et al. | 606/86 A |
| 2008/0312704 A1 * | 12/2008 | Hestad et al. | 606/86 A |
| 2008/0319477 A1 | 12/2008 | Justis et al. | |
| 2009/0062858 A1 * | 3/2009 | Dziedzic et al. | 606/278 |
| 2009/0264930 A1 | 10/2009 | McBride | |
| 2009/0326586 A1 * | 12/2009 | Duarte | 606/264 |
| 2010/0076502 A1 * | 3/2010 | Guyer et al. | 606/86 R |
| 2010/0222828 A1 * | 9/2010 | Stad et al. | 606/86 A |
| 2011/0022088 A1 * | 1/2011 | Forton et al. | 606/246 |

* cited by examiner

*Primary Examiner* — Mary Hoffman

(57) ABSTRACT

One nonlimiting embodiment of the present application is directed to a system for positioning a connecting element adjacent one or more bones or bony portions, such as the spinal column, through a minimally invasive surgical approach. The system generally includes a number of bone anchors engageable to the one or more bones or bony portions and a number of anchor extenders removably engaged to the bone anchors. An inserter instrument is removably positioned adjacent to one of the anchor extenders and is operable to position a connecting element engaged thereto to a location adjacent the number of bone anchors in a minimally invasive surgical procedure. However, in other embodiments, different forms and applications are envisioned.

14 Claims, 15 Drawing Sheets

SYSTEMS AND METHODS FOR MINIMALLY INVASIVE STABILIZATION OF BONY STRUCTURES

BACKGROUND

Various devices and methods for stabilizing bone structures have been used for many years. For example, the fracture of an elongated bone, such as a femur or humerus, can be stabilized by securing a plate to the fractured bone across the fracture. The plate extends across the fractured area and thus stabilizes the fractured components of the bones relative to one another in a desired position. When the fracture heals, the plate can be removed or left in place, depending on the type of plate that is used.

Another type of stabilization technique uses one or more elongated rods extending between components of a bony structure and secured to the bony structure to stabilize the components relative to one another. The components of the bony structure are exposed and one or more bone engaging fasteners are placed into each component. The elongated rod is then secured to the bone engaging fasteners in order to stabilize the components of the bony structure.

One problem associated with the above described stabilization structures is that the skin and tissue surrounding the surgical site must be cut, removed, and/or repositioned in order for the surgeon to access the location where the stabilization device is to be installed. This repositioning of tissue causes trauma, damage, and scarring to the tissue. There are also risks that the tissue will become infected and that a long recovery time will be required after surgery for the tissue to heal.

Minimally invasive surgical techniques are particularly desirable in, for example, spinal and neurosurgical applications because of the need for access to locations deep within the body and the presence of vital intervening tissues. The development of percutaneous minimally invasive spinal procedures has yielded a major improvement in reducing recovery time and post-operative pain because they require minimal, if any, muscle dissection and can be performed under local anesthesia. These benefits of minimally invasive techniques have also found application in surgeries for other locations in the body where it is desirable to minimize tissue disruption and trauma. However, there remains a need for further improvements in instruments, systems and methods for stabilizing bony structures using minimally invasive techniques.

SUMMARY

One nonlimiting embodiment of the present application is directed to a system for positioning a connecting element adjacent one or more bones or bony portions, such as the spinal column, through a minimally invasive surgical approach. The system generally includes a number of bone anchors engageable to the one or more bones or bony portions and a number of anchor extenders removably engaged to the bone anchors. An inserter instrument is removably positioned adjacent to one of the anchor extenders and is operable to position a connecting element engaged thereto to a location adjacent the number of bone anchors in a minimally invasive surgical procedure. However, in other embodiments, different forms and applications are envisioned.

For example, another embodiment of the subject application is directed to a system for minimally invasive surgery that includes at least one bone anchor that has a distal bone engaging portion and a proximal receiving portion. The system further includes at least one extender including a body extending between a proximal end portion and a distal end portion configured to releasably engage with the at least one bone anchor, and a mounting assembly releasably engageable with the proximal end portion of the at least one extender. The mounting assembly also includes a receiving portion. An inserter instrument including a guide member and a connecting element engaging member axially movable relative to the guide member are also provided in the system. Moreover, the inserter instrument is positionable in the receiving portion of the mounting assembly with the guide member positioned adjacent to the extender such that the guide member guides a connecting element toward the proximal receiving portion of the at least one bone anchor as the rod engaging member is moved distally.

In yet another embodiment, a system for minimally invasive surgery includes at least one bone anchor including a distal bone engaging portion and a proximal receiving portion. The system further includes at least one extender that has a body extending along a longitudinal axis between a proximal end portion and a distal end portion configured to releasably engage with the at least one bone anchor. An inserter instrument positionable adjacent to and alongside the at least one extender is also provided in the system. The inserter instrument includes an elongated housing extending along a longitudinal axis between a proximal end and a distal end. The elongated housing includes an internal chamber that terminates distally at a distal surface and also includes a lateral opening extending through a side portion of the elongated housing. A connecting element engaging member communicates with the internal chamber and includes a distal end portion configured to engage with a connecting element. The connecting element engaging member is operable to move the connecting element distally into engagement with the distal surface and the distal surface is configured to change an orientation of the connecting element and guide the connecting element through the lateral opening toward the proximal receiving portion of the at least bone anchor as the connecting element engaging member is moved distally.

In another embodiment, a system for minimally invasive surgery includes at least one bone anchor that has a distal bone engaging portion and a proximal receiving portion. The system also includes at least one extender including a body extending along a longitudinal axis between a proximal end portion and a distal end portion configured to releasably engage with the at least one bone anchor. The system also includes an inserter instrument that has an elongated body extending between a proximal end and a distal end. A passage is defined by the elongated body and is distally bound by a distal surface. The inserter instrument also includes a connecting element engaging member pivotally mounted to and axially movable relative to the elongated body. The connecting element engaging member also includes a distal end portion configured to engage with a connecting element. In addition, the connecting element engaging member is operable to move the connecting element distally into engagement with the distal surface, and the passage and the distal surface are configured to guide the connecting element toward the proximal receiving portion of the at least bone anchor as the connecting element engaging member is moved distally and pivoted toward the elongated body.

Another embodiment of the present application is a unique system for minimally invasive surgery in a patient. Other embodiments include unique methods, systems, devices, kits, assemblies, equipment, and/or apparatus involving minimally invasive surgical systems and techniques.

Further embodiments, forms, features, aspects, benefits, objects and advantages of the present application shall become apparent from the detailed description and figures provided herewith.

DESCRIPTION OF THE ILLUSTRATED EMBODIMENTS

Figure 1:
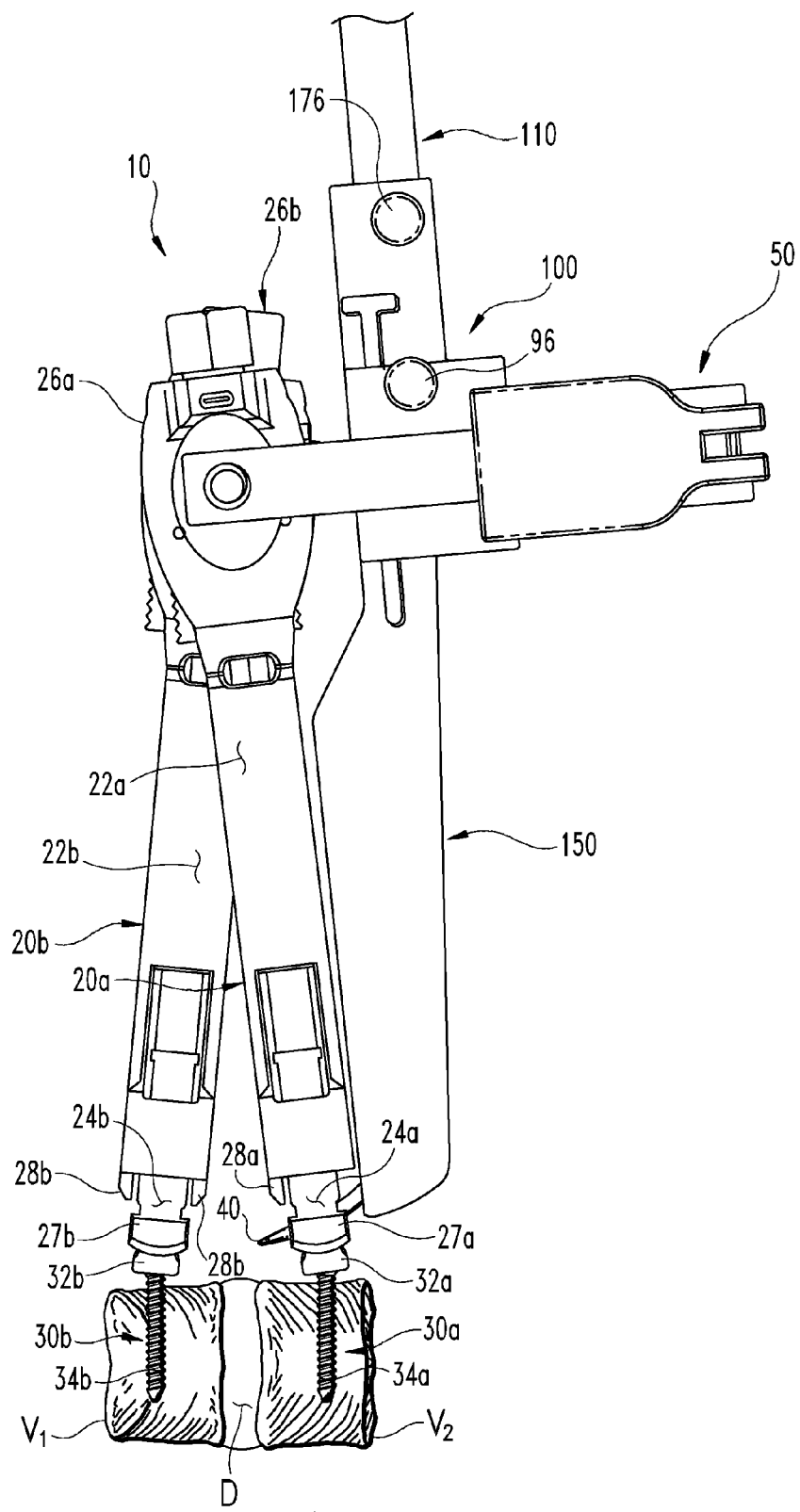
FIG. 1 is a perspective view of a system for positioning a connecting element in a patient in minimally invasive surgical procedures.
Figure 2:
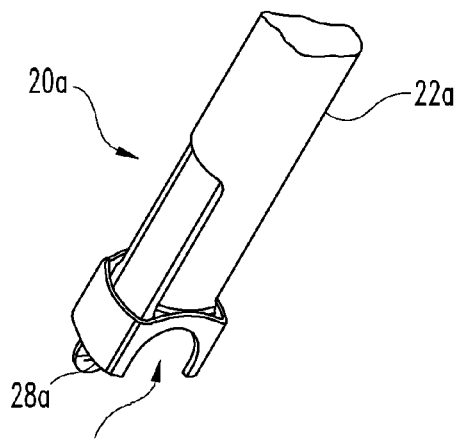
FIG. 2 is an enlarged, perspective view of a portion of an anchor extender of the system illustrated in FIG. 1.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

The subject application is generally directed to systems for positioning a connecting element adjacent one or more bones or bony portions, such as the spinal column, through a minimally invasive surgical approach. The systems generally include a number of bone anchors engageable to the one or more bones or bony portions and a number of anchor extenders removably engaged to the bone anchors. An inserter instrument is removably positioned adjacent to one of the anchor extenders and is operable to position a connecting element engaged thereto to a location adjacent the number of bone anchors in a minimally invasive surgical procedure. In one aspect, the inserter instrument is positioned alongside the anchor extender and in the same incision through tissue and muscle in which the anchor extender is positioned. In addition, applications in non-minimally invasive surgeries are also contemplated.

Referring now to FIG. 1, there is shown a minimally invasive surgical system 10 that is positioned relative to a portion of the spinal column including adjacent vertebrae $V_1$, $V_2$ and a disc D positioned therebetween. It should be appreciated that use of system 10 at other anatomical locations besides the spinal column are also contemplated. System 10 includes two anchor extenders 20a, 20b releasably mountable to respective ones of anchors 30a, 30b, a connecting element 40, a mounting assembly 50 engaged with anchor extenders 20a, 20b, and an inserter instrument 100. Anchors 30a, 30b include proximal receiving portions 32a, 32b configured to receive connecting element 40 and a distal bone engaging portion 34a, 34b. In the illustrated embodiment, bone engaging portions 34a, 34b are bone screws with a threaded shank to engage the bony structure of the underlying vertebrae $V_1$, $V_2$. Proximal receiving portions 32a, 32b are receivers having a pair of opposing arms defining a longitudinal passage. The arms further define a proximal/distally extending opening that opens at a proximal end of the arms to receive a set screw (not shown) to secure connecting element 40 in the passage. Bone engaging portions 34a, 34b can be pivotally received in proximal receiving portions 32a, 32b through the distal openings thereof, and structured to interact therewith to provide anchors 30a, 30b with multi-axial capabilities that permit either a selected number of positions or infinitely numbered of positions of bone engaging portions 34a, 34b relative to proximal receiving portions 32a, 32b.

Other forms for anchors 30a, 30b are contemplated, including uni-axial and uni-planar forms. The bone engaging portion can also be in the form of a spike, staple, hook, fusion device, cannulated screw, fenestrated screw, interbody device, intrabody device, clamp, plate, suture anchor, bolt, pin or other bone engaging member. The receiving portion can be in the form of a saddle, yoke, eye-bolt or through-hole, side opening member, bottom opening member, top-opening member, eyelet, or any other structure engageable to connecting element 40.

In the illustrated embodiment, connecting element 40 is a rigid rod curved along an arc between its ends. However, it is contemplated that connecting element 40 can have a curvature that varies or is compounded along its length, or could be linear. In addition, in other forms it is contemplated that connecting element 40 can include any configuration known for a rod, implant, or fastener, so long as connecting element 40 is insertable using inserter instrument 100 in order to stabilize adjacent vertebrae $V_1$, $V_2$. Further, it is contemplated that connecting element 40 can be non-rigid, elastic and/or super-elastic and in the form of a cable, band, wire, or artificial ligament that is used in tethering, guiding, or other surgical procedures. In addition, in the illustrated form connecting element 40 tapers to a point at each of its ends such that the ends each include a generally conical configuration. However, it should be appreciated that other configurations for the ends of connecting element 40 are contemplated.

Anchor extenders 20a, 20b each extend between a proximal end portion 26a, 26b and a distal end portion 27a, 27b and include an elongated inner member 24a, 24b engageable to anchors 30a, 30b, respectively. Anchor extenders 20a, 20b also include outer member assemblies 22a, 22b positioned about and engaged to inner members 24a, 24b, respectively. Outer member assemblies 22a, 22b are operable to manipulate inner members 24a, 24b to a first condition or position permitting anchors 30a, 30b to be loaded or ejected from inner members 24a, 24b, a second condition or position where anchors 30a, 30b are securely engaged to inner members 24a, 24b, and a plurality of reduced conditions or positions where inner members 24a, 24b and outer member assemblies 22a, 22b are axially displaced relative to one another to manipulate vertebrae $V_1$, $V_2$ engaged to anchors 30a, 30b and/or to position connecting element 40 into anchors 30a, 30b while inner members 24a, 24b remain engaged to anchors 30a, 30b. With particular regard to outer assembly 22b, it includes a pair of oppositely positioned and distally extending tabs 28b (only one of which is illustrated in FIG. 1) which are structured to engage with connecting element 40 when outer member assemblies 22a, 22b are axially displaced relative to inner members 24a, 24b to position connecting element 40 into anchors 30a, 30b. In contrast to outer member assembly 22b, outer member assembly 22a includes a proximally extending slot 29 positioned opposite of a distally extending tab 28a configured similar to tab 28b of outer member assembly 22b. Slot 29 generally provides additional clearance for connecting element 40 as it is positioned adjacent to anchors 30a, 30b from inserter instrument 100, further details of which will be provided below. In other non-illustrated forms however, it is contemplated that outer member assembly 22a could be provided with a pair of distally extending tabs similar to outer member assembly 22b. Further details regarding the general structure and function of anchor extenders 20a, 20b are provided in U.S. Patent Publication No. 2008/0319477 to Justis et al., the contents of which are incorporated herein by reference in their entirety. However, it should be appreciated that alternatively configured anchor extenders are also contemplated for use in the systems disclosed in this document so long as they facilitate engagement with mounting assembly 50 and introduction of connecting element 40 adjacent to anchors 30a, 30b.

Figure 3:
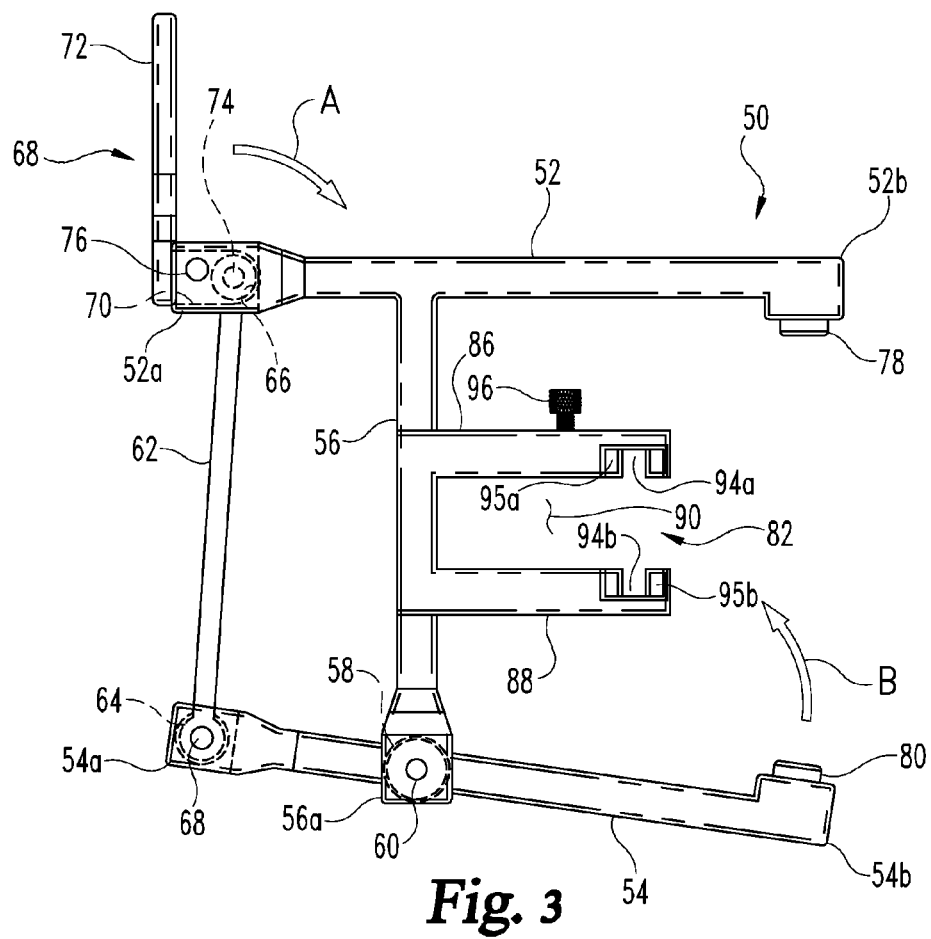
FIGS. 3 and 4 are top plan views illustrating a mounting assembly of the system illustrated in FIG. 1 between open and closed configurations for engaging with the anchor extenders illustrated in FIG. 1.
Figure 4:
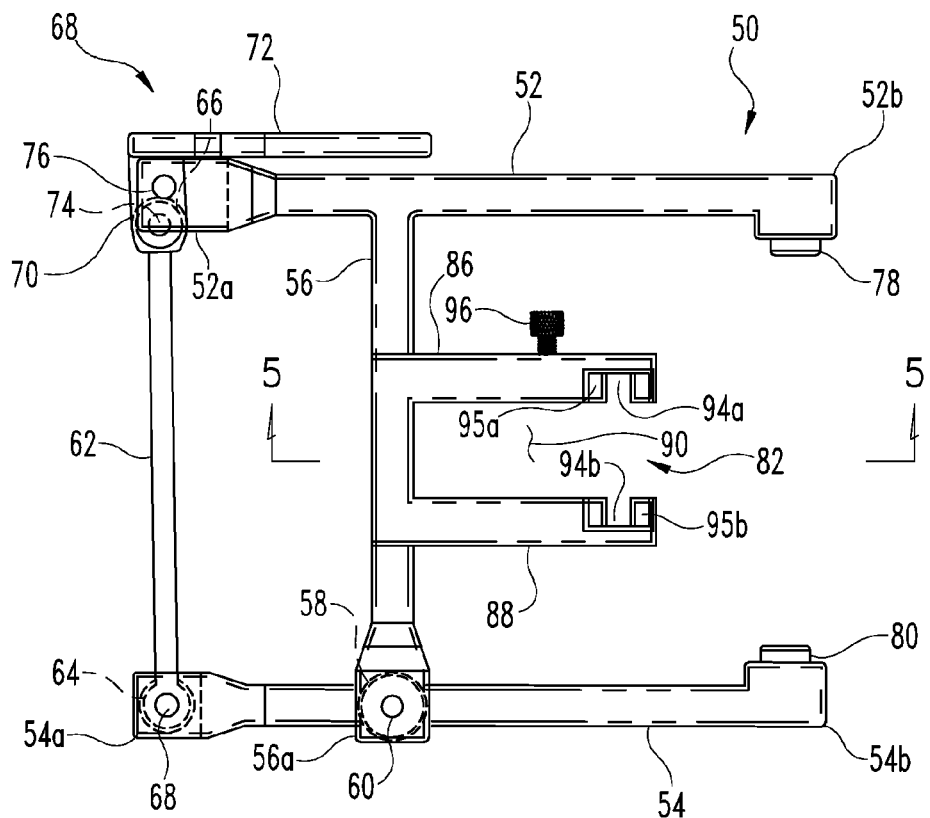

Referring now further to FIGS. 3 and 4, mounting assembly 50 is shown in a top, plan view positioned between an open configuration in FIG. 3 to facilitate positioning of mounting assembly 50 relative to proximal end portions 26a, 26b of anchor extenders 20a, 20b and a closed configuration in FIG. 4 to facilitate engagement of mounting assembly 50 with proximal end portions 26a, 26b of anchor extenders 20a, 20b. Mounting assembly 50 generally includes a first engaging arm 52 that extends between a first end 52a and a second end 52b and is positioned opposite of a second engaging arm 54 that extends between a first end 54a and a second end 54b. An intermediate arm 56 extends between first engaging arm 52 and second engaging arm 54 and is positioned between first ends 52a, 54a and second ends 52b, 54b. In this configuration, mounting assembly 50 is generally provided with a U-shape when viewed from above as in FIGS. 3 and 4.

Intermediate arm 56 extends from first engaging arm 52 to an end portion 56a to which second engaging arm 54 is pivotally coupled between first end 54a and second end 54b. More particularly, in the illustrated form, second engaging arm 54 includes an enlarged portion 58 which is received in end portion 56a of intermediate arm 56 and coupled thereto with pin 60. First end 54a of second engaging arm 54 is also pivotally coupled with a linking arm 62 that extends between first engaging arm 52 and second engaging arm 54. More particularly, linking arm 62 includes an enlarged end portion 64 that is received in first end 54a and coupled thereto with pin 68. The opposite end 66 of linking arm 62 is pivotally coupled to body portion 70 of cam member 68 by pin 74. Body portion 70 of cam member 68 is positioned in and pivotally coupled to first end 52a of first engaging arm 52 by pin 76.

In this configuration, as handle portion 72 of cam member 68 is pivoted about pin 76 toward first engaging arm 52 as indicated by directional arrow A in FIG. 3, the arrangement of body portion 70 of cam member 68 relative to first engaging arm 52 changes such that linking arm 62 is forced away from first engaging arm 52. In turn, second engaging arm 54 pivots about pin 68 relative to enlarged end portion 64 of linking arm 62 and about pin 60 relative to intermediate arm 56 such that second end 54b of second engaging arm is moved toward second end 52b of first engaging arm 52 as indicated by directional arrow B in FIG. 3. Handle portion 72 can be pivoted until it is flush alongside first engaging arm 52 as illustrated in FIG. 4 and anchor extenders 20a, 20b (not shown) are secured between second ends 52b, 54b. In the illustrated form, second ends 52b, 54b are provided with projections 78, 80 that are configured to engage with corresponding receptacles (not shown) in proximal end portions 26a, 26b or anchor extenders 20a, 20b. Other arrangements contemplate that each of first and second engaging arms 52, 54 includes a receptacle and that each of proximal end portions 26a, 26b includes a corresponding projection. In the illustrated form, projections 78, 80 are provided with a generally cylindrical configuration, although it should be appreciated that in alternative forms projections 78, 80 could be provided with a square or rectangular shape or be otherwise configured to provide a keyed relationship between projections 78, 80 and the receptacles on anchor extenders 20a, 20b. In addition, while not illustrated it should be appreciated that mounting assembly 50 could be provided with a latch or similar structure configured to releasably retain handle portion 72 adjacent to first engaging arm 52 when mounting assembly 50 is engaged with anchor extenders 20a, 20b.

Figure 5:
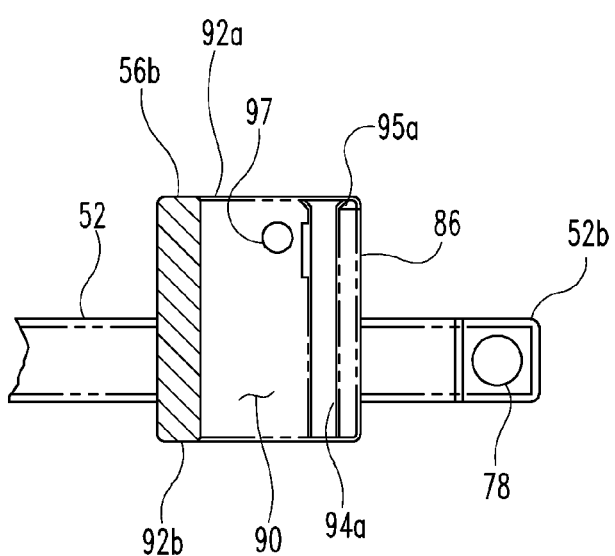
FIG. 5 is a section view along view line 5-5 of FIG. 4.

Referring now generally to FIGS. 3-5, mounting assembly 50 also includes a receiving portion 82 positioned along intermediate arm 56 between first and second engaging arms 52, 54. Receiving portion 82 is generally structured to receive and engage with inserter instrument 100. In one form, receiving portion 82 is positioned between first and second engaging arms 52, 54 such that inserter instrument 100, when engaged with receiving portion 82, is aligned with a central plane extending between anchor extender 20a and anchor extender 20b. Receiving portion 82 is generally U-shaped and is defined by a pair of branches 86, 88 that extend from intermediate arm 56, and intermediate arm 56 includes an enlarged portion 56b between branches 86, 88. Branches 86, 88 define a channel 90 that extends between a proximal surface 92a and a distal surface 92b and is generally configured to receive inserter instrument 100. Channel 90 includes a pair of oppositely positioned slots 94a, 94b formed in branches 86, 88, respectively, and extending between proximal surface 92a and distal surface 92b. Each of slots 94a, 94b includes a proximal portion 95a, 95b that is enlarged relative to the remainder of the slots 94a, 94b. In this configuration, slots 94a, 94b are configured to cooperate with projections on inserter instrument 100 to maintain inserter instrument 100 in a certain orientation and limit distal movement of inserter instrument 100 in channel 90. Otherwise, it should be appreciated that inserter instrument 100 is axially slidable along channel 90 to a number of different positions relative to receiving portion 82. However, receiving portion 82 is also provided with a locking member 96, such as a set screw, that is positioned in a through-bore 97 communicating with channel 90 in order to facilitate locking the axial position of inserter instrument 100 relative to receiving portion 82.

As illustrated in FIG. 1, inserter instrument 100 generally includes a connecting element engaging member 110 and an elongated housing 150. Further details regarding engaging member 110 are illustrated in FIGS. 6-9. More particularly, engaging member 110 includes an elongated shaft portion 112 extending along a longitudinal axis L between a proximal end portion 114 and a distal end portion 116. In the illustrated form, shaft portion 112 includes a rectangular configuration, although it should be appreciated that alternative configurations and shapes for shaft portion 112 are contemplated. For example, shaft portion 112 could be square, circular or triangular, just to provide a few possibilities. Shaft portion 112 also includes a pair of distally extending flanges 118, 120 positioned adjacent to distal end portion 116. A coupling portion 122 is positioned between flanges 118, 120 and is pivotally coupled to elongated shaft portion 112 by pin 124.

Figure 7:
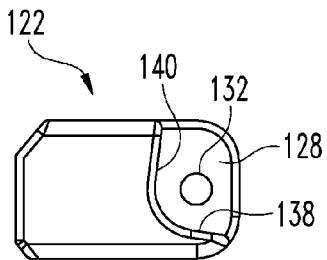
FIG. 7 is an enlarged, side plan view of the coupling portion of the engaging member of FIG. 6.
Figure 8:
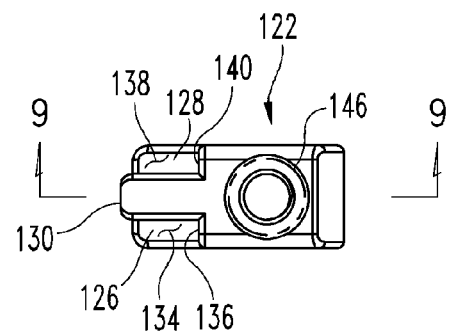
FIG. 8 is a top plan view of the coupling portion illustrated in FIG. 7.

More particularly, as illustrated in FIGS. 7 and 8, coupling portion 122 includes a pair of recesses 126, 128 positioned on opposite sides of a reduced thickness portion 130 of coupling portion 122, and a bore 132 extends through portion 130. In this configuration, portion 130 is positioned between flanges 118, 120, and flanges 118, 120 are positioned in recesses 126, 128 when coupling portion 122 is coupled to elongated shaft portion 112 with pin 124. In addition, coupling portion 122 includes bearing surfaces 134, 136 which extend around recess 126 and bearing surfaces 138, 140 which extend around recess 128. Surfaces 134, 138 and 136, 140 limit the range of pivotal motion of coupling portion 122 relative to elongated shaft portion 112. More particularly, as coupling portion 122 is pivoted toward longitudinal axis L of elongated shaft portion 112, surfaces 134, 138 bear against flanges 118, 120 until further movement of coupling portion 122 toward longitudinal axis L of elongated shaft portion 112 is prevented. Similarly, as coupling portion 122 is pivoted away from longitudinal axis L of elongated shaft portion 112, surfaces 136, 140 bear against flanges 118, 120 until further movement of coupling portion 122 away from longitudinal axis L of elongated shaft portion 112 is prevented. In one form, it is contemplated that coupling portion 122 generally extends along longitudinal axis L when further pivoting of it toward longitudinal axis L is prevented, and that coupling portion 122 generally extends perpendicularly to longitudinal axis L when further pivoting of it away from longitudinal axis L is prevented. Similarly, it should be appreciated that this configuration generally provides a ninety degree range of pivotal movement of coupling portion 122 relative to longitudinal axis L. However, it is contemplated that coupling portion 122 and/or flanges 118, 120 could be alternatively configured to provide a different range of motion of coupling portion 122 relative to longitudinal axis L.

Figure 6:
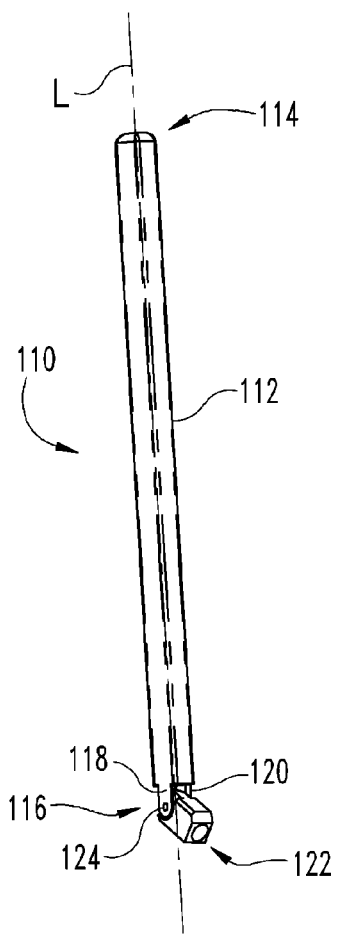
FIG. 6 is a perspective view of a connecting element engaging member of the inserter instrument illustrated in FIG. 1.
Figure 9:
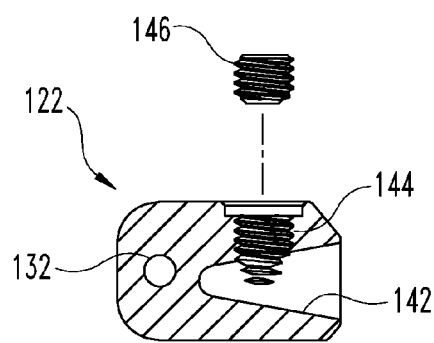
FIG. 9 is a section view along view line 9-9 of FIG. 8.
Figure 10:
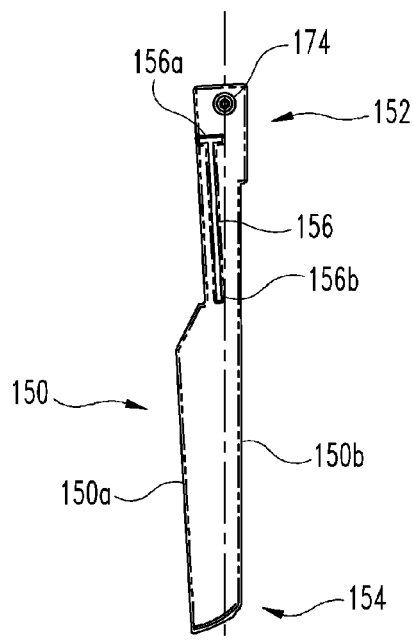
FIG. 10 is a plan view of the elongated housing of the inserter instrument illustrated in FIG. 1.
Figure 11:
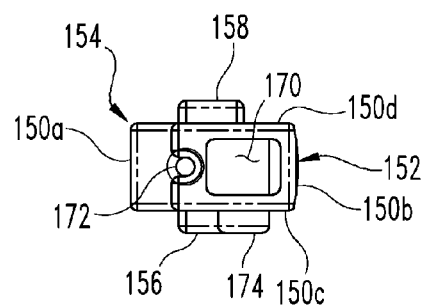
FIG. 11 is a top plan view of the elongated housing illustrated in FIG. 10.

Coupling portion 122 is also configured to securely engage with connecting element 40. More particularly, as illustrated in FIGS. 6 and 9, coupling portion 122 includes an internal receptacle 142 into which an end portion of connecting element 40 can be positioned. As indicated above, the end portions of connecting element 40 have a generally conical external configuration. Similarly, in the illustrated form, internal receptacle 142 includes a generally conical internal configuration that corresponds to the external configuration of the ends of connecting element 40. In other non-illustrated forms, it is contemplated that internal receptacle 142 and the ends of connecting element 40 can be provided with other corresponding configurations, although embodiments in which the configurations of internal receptacle 142 and the ends of connecting element 40 do not correspond to one another can also be used so long as coupling portion 122 is still able to securely engage with connecting element 40. Coupling portion 122 also includes a transverse bore 144 that is internally threaded to receive an externally threaded locking member 146. In this arrangement, locking member 146 may be advanced into bore 144 to provide a locking force on connecting element 40 in order to securely engage coupling portion 122 with connecting element 40. Once connecting element 40 has been inserted with inserter instrument 100, locking member 146 may be separated from connecting element 40 in order to facilitate disengagement between connecting element 40 and coupling portion 122. While, locking member 146 and bore 144 are provided with a threaded arrangement, it should be appreciated that alternative configurations for securely coupling coupling portion 122 with connecting element 40 are contemplated. For example, in one non-limiting and non-illustrated form, one or more of the ends of connecting element 40 can be provided with a notched section and coupling portion 122 can be provided with a closing assembly, such as a scissor mechanism or a linear slide mechanism, that is configured to engage around the notched portion in order to securely engage coupling portion 122 with connecting element 40.

Referring now generally to FIGS. 10-13, elongated housing 150 of inserter instrument 100 generally extends along a longitudinal axis L between a proximal end portion 152 and a distal end portion 154 and includes a plurality of external surfaces 150a, 150b, 150c, 150d. Proximal end portion 152 of elongated housing 150 is generally configured to be received in channel 90 of receiving portion 82 of mounting assembly 50. Similarly, as indicated above, proximal end portion 152 includes a pair of generally T-shaped projections 156, 158 configured to be positioned in and received by slots 94a, 94b of channel 90. More particularly, distal end portions 156b, 158b of projections 156, 158 can be aligned with and inserted into enlarged proximal portions 95a, 95b of slots 94a, 94b and then advanced along slots 94a, 94b to position elongated housing 150 into receiving portion 82. Elongated housing 150 can be moved distally relative to receiving portion 82 to move proximal end portions 156a, 158a of projections 156, 158 toward proximal portions 95a, 95b of slots 94a, 94b. However, proximal portions 156a, 158a are generally configured to be received in and cooperate with proximal portions 95a, 95b of slots 94a, 94b to limit distal movement elongated housing 150 relative to receiving portion 82. In addition, it should be appreciated that engagement between projections 156, 158 and slots 94a, 94b may also eliminate or reduce rocking motion of elongated housing 150 relative to receiving portion 82. Moreover, once elongated housing 150 is positioned in receiving portion 82, locking member 96 can be used to selectively lock elongated housing 150 at any one of a plurality of axial positions relative to receiving portion 82.

Figure 12:
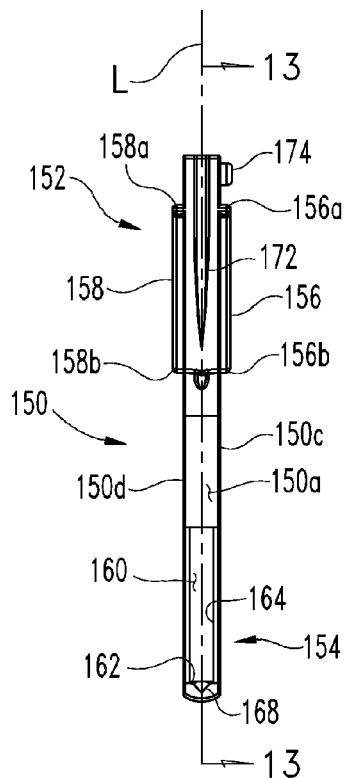
FIG. 12 is a plan view of the elongated housing illustrated in FIG. 10 rotated ninety degrees.

In the illustrated embodiment, distal end portion 154 is generally arcuate or rounded in order to eliminate interference between elongated housing 150 and adjacent tissue and/or muscle as elongated housing 150 is positioned at a surgical site. Elongated housing 150 also includes an internal chamber 160 positioned adjacent to distal end portion 154. Internal chamber 160 is distally bound by a distal surface 162 that extends transversely to longitudinal axis L. In one or more forms, it is contemplated that distal surface 162 may also be provided with an arcuate or partially arcuate configuration. As illustrated in FIG. 12, distal surface 162 also includes a groove 168 that narrows toward longitudinal axis L and is obliquely angled relative to distal surface 162. Groove 168 and distal surface 162 are both arranged to assist in guiding connecting element 40 as it is installed with inserter instrument 100. Similarly, during use, it should be appreciated that elongated housing 150 serves as a guide member for connecting element 40. Further details regarding these features will be discussed below in connection with FIGS. 14-19. Internal chamber 160 is surrounded and enclosed by surfaces 150b, 150c, and 150d of elongated housing 150, but includes a lateral opening 164 extending through surface 150a of elongated housing 150. In other forms, it is contemplated that internal chamber 160 could be provided with one or more additional openings through one or more of surfaces 150a, 150b, 150c, 150d.

An elongated passage 170 communicates with internal chamber 160 and opens through proximal end 152 of elongated housing 150. Passage 170 is laterally offset from the center of internal chamber 160 and includes a rectangular configuration that generally has a smaller cross-sectional dimension between surfaces 150c and 150d of elongated housing 150 relative to a corresponding cross-sectional dimension of internal chamber 160. Passage 170 is generally configured to receive at least a portion of engaging member 110 in an axially movable or slidable relationship relative to one another. Moreover, as indicated above, elongated shaft portion 112 of engaging member 110 also has a rectangular configuration. Likewise, when positioned in passage 170, engaging member 110 will be non-rotatably constrained relative to elongated housing 150. However, it should be appreciated that alternative configurations for preventing rotation between engaging member 110 and elongated housing 150 are contemplated. In addition, in one or more non-illustrated forms, it is also contemplated that member 110 may be rotatable relative to elongated housing 150 when it is positioned in passage 170.

Figure 13:
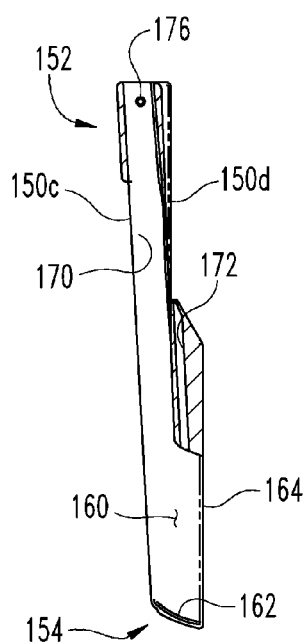
FIG. 13 is a section view along view line 13-13 of FIG. 12.

Elongated housing 150 also includes a locking member 174, such as a set screw, positioned adjacent to proximal end portion 152 and in engagement with a bore 176 extending into communication with elongated passage 170. In this configuration, locking member 174 may be advanced through bore 176 into contact with elongated housing 150 in order to axially restrain engaging member 110 relative to elongated housing 150 at any one of a plurality of possible configurations. In addition, elongated housing 150 is also provided with a second elongated passage 172 that generally extends parallel to passage 170, although non-parallel configurations between passages 170 and 172 are contemplated. As illustrated in FIGS. 12 and 13, passage 172 is only partially enclosed adjacent to proximal end 152 of elongated housing 150 and defines a partially arcuate groove in surface 150a. However, adjacent to internal chamber 160, passage 172 is completely enclosed by elongated housing 150. Passage 172 communicates with internal chamber 160 and is generally configured to allow access to locking member 146 of coupling portion 122 with an instrument, such as a screwdriver, when coupling portion 122 is positioned in internal chamber 160, further details of which will be provided below.

Figure 14:
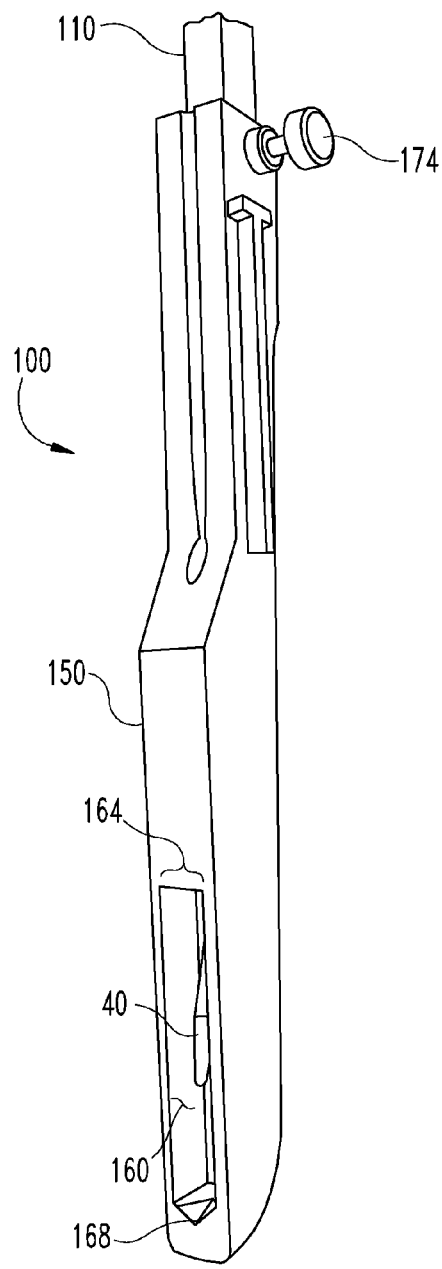
FIGS. 14 and 15 are perspective views illustrating distal movement of a connecting element in the inserter instrument illustrated in FIG. 1.

FIGS. 1 and 14-19 generally illustrate various steps of inserting connecting element 40 with inserter instrument 100 of system 10. In FIG. 14 for example, connecting element 40 is coupled with coupling portion 122 of engaging member 110 and is positioned in internal chamber 160 of elongated housing 150. In this arrangement, connecting element 40 generally extends in-line with longitudinal axis L of elongated housing 150. In one form, connecting element 40 may be coupled with coupling portion 122 by moving engaging member 110 to its distal most position in elongated housing 150 which directs internal receptacle 142 toward lateral opening 164 so that an end of connecting element 40 may be positioned therein. Further, in this position of engaging member 110, locking member 146 of coupling portion 122 is generally aligned with and faces elongated passage 172 such that an instrument (not shown), such as a screwdriver, can be advanced through passage 172 into engagement with locking member 146. The instrument may then be rotated to advance and tighten locking member 146 against connecting element 40 in order to securely retain connecting element 40 in internal receptacle 146 of coupling portion 122. Alternatively, it is contemplated that connecting element 40 could be coupled with coupling portion 122 before engaging member 110 is positioned in passage 170 of elongated housing 150. For example, in this form, connecting element 40 may be inserted into passage 170 until it is positioned in internal chamber 160 as illustrated in FIG. 14. As indicated above, connecting element 40 in the illustrated form is generally curved along an arc between its opposite ends. Similarly, as illustrated in FIG. 14, connecting element 40 can be arranged relative to elongated housing 150 such that the concave side of connecting element 40 is oriented toward lateral opening 164 in order to assist in guidance of connecting element 40 from internal chamber 160, further details of which are provided below.

With connecting element 40 positioned in internal chamber 160 as illustrated in FIG. 14, locking member 174 may be tightened against engaging member 110 to fix engaging member 110 relative to elongated housing 150. Inserter instrument 100 may then also be positioned in receiving portion 82 of mounting assembly 50 either before or after it has been engaged with proximal end portions 26a, 26b of anchor extenders 20a, 20b. As another variation, it is also contemplated that elongated housing 150 could be positioned in receiving portion 82 followed by positioning connecting element 40 and engaging member 110 into passage 170 through proximal end 152 of elongated housing 150. As illustrated in FIGS. 1 and 16-19, elongated housing 150 of inserter instrument 100 generally extends alongside anchor extender 20a when it is positioned in receiving portion 82 of mounting assembly 50 and mounting assembly 50 is engaged with anchor extenders 20a, 20b. In addition, lateral opening 164 is oriented toward anchor extender 20a in this arrangement. Elongated housing 150 of inserter instrument 100 may be advanced distally toward anchor 30a until lateral opening 164 is generally aligned with slot 29 of outer member assembly 22a of anchor extender 20a. It should also be appreciated that lateral opening 164 may also be generally aligned with a distal slot in inner members 22a, 22b of anchor extenders 20a, 20b and/or proximal receiving portions 32a, 32b of anchors 30a, 30b. In addition, in one or more forms, positioning of elongated housing 150 alongside anchor extender 20a may be performed in the same incision through which anchor extender 20a extends into engagement with anchor 30a. Once initial positioning of elongated housing 150 is achieved, locking member 96 may be tightened against elongated housing 150 to fix elongated housing 150 relative to mounting assembly 50 at a desired axial position.

Figure 15:
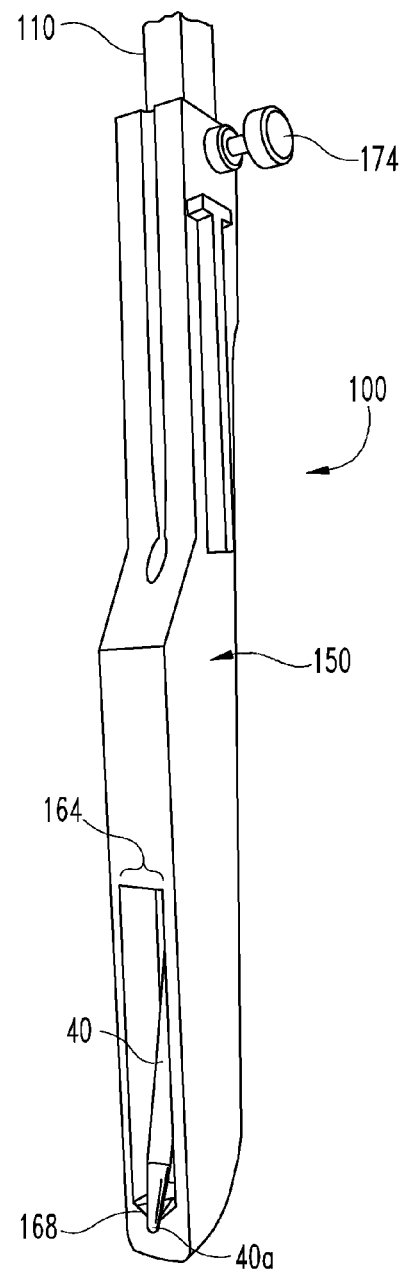

FIG. 15 illustrates initial distal movement of engaging member 110 relative to elongated housing 150, and corresponding initial distal movement of connecting element 40 in internal chamber 160. It should be appreciated that the movement illustrated in FIG. 15 could be performed either before or after inserter instrument 100 is position in mounting assembly 50. However, if this movement is performed before inserter instrument 100 is positioned in mounting assembly 50, it should be appreciated that retaining end 40a of connecting element 40 within internal chamber 160 may be desirable in order to avoid interference with anchor extender 20a, anchor 30a and/or surrounding patient tissue or other anatomical features as inserter instrument 100 is positioned alongside anchor extender 20a. As connecting element 40 is moved distally in internal chamber 160, its end 40a comes into contact with distal surface 162 which further guides end 40a into groove 168. Upon further distal movement of engaging member 110 and connecting element 40, end 40a of connecting element 40 continues along groove 168 until it extends through lateral opening 164. As this occurs, distal surface 162 and groove 168 begin guiding connecting element 40 toward anchor extender 20a and anchor 30a, and coupling portion 122 pivots away from the longitudinal axis L of elongated shaft portion 112 of engaging member 110 such that the orientation of connecting element 40 relative to elongated housing 150 begins to change.

Figure 16:
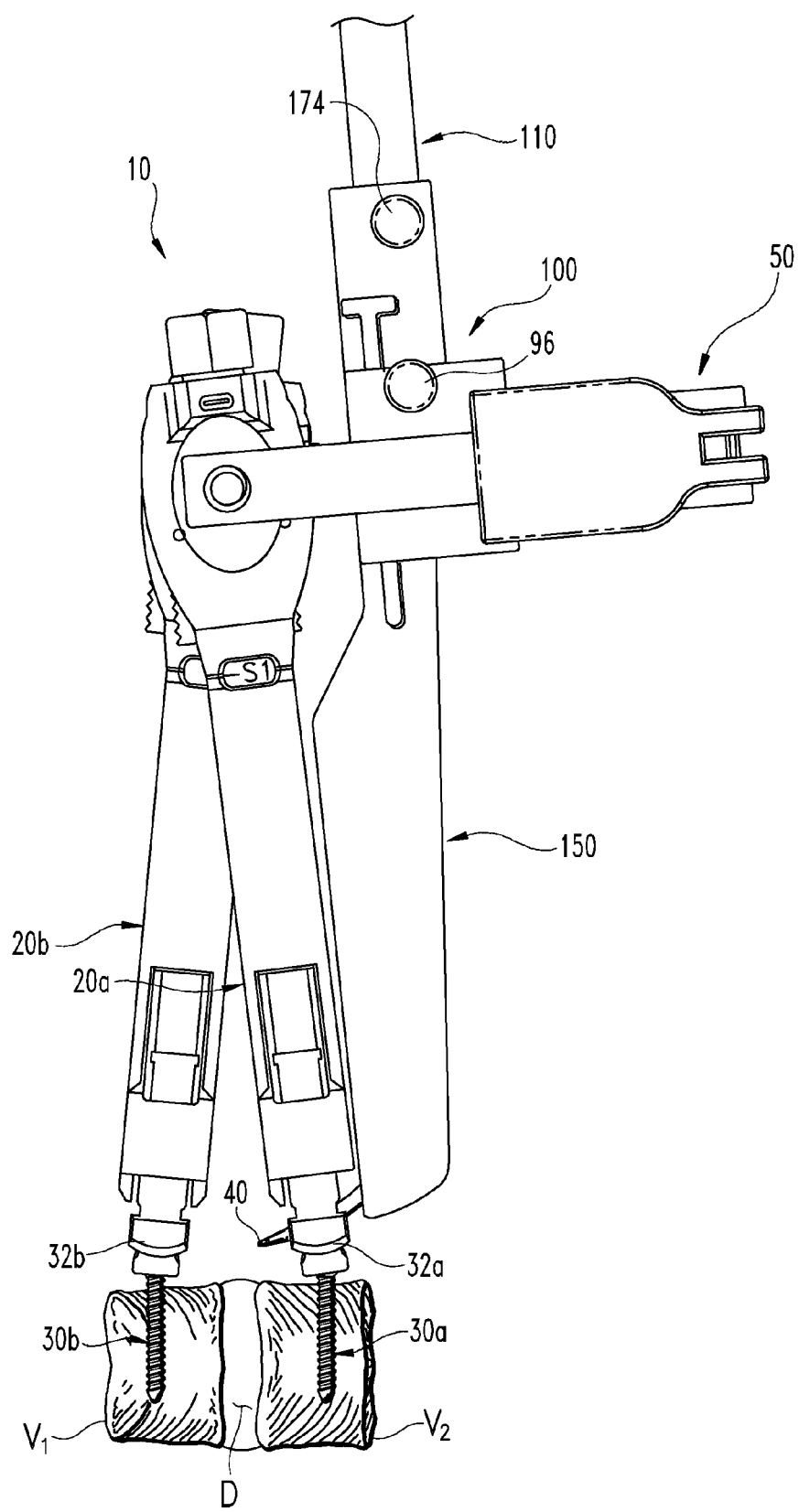
FIGS. 16-19 illustrate various steps of a minimally invasive surgical procedure for inserting a connecting element with the system illustrated in FIG. 1.

As illustrated in FIGS. 1 and 16, upon additional distal movement of engaging member 110 relative to elongated housing 150, distal surface 162 and groove 168 continue to guide connecting element 40 from internal chamber 160 toward proximal receiving portions 32a, 32b of anchors 30a, 30b. Similarly, coupling portion 122 also pivots further away from the longitudinal axis L of elongated shaft portion 112 of engaging member 110 such that the orientation of connecting element 40 relative to elongated housing 150 continues to change. As also illustrated in FIGS. 1 and 16, connecting element 40 extends at an oblique angle relative to vertebrae $V_1, V_2$ as it is inserted through anchor 30a toward anchor 30b. Among other things, this arrangement may allow end 40a of connecting element 40, and eventually connecting element 40, to extend through and/or below tissue between anchors 30a, 30b in order to allow positioning of connecting element 40 while avoiding cutting and/or removing this tissue.

Figure 17:
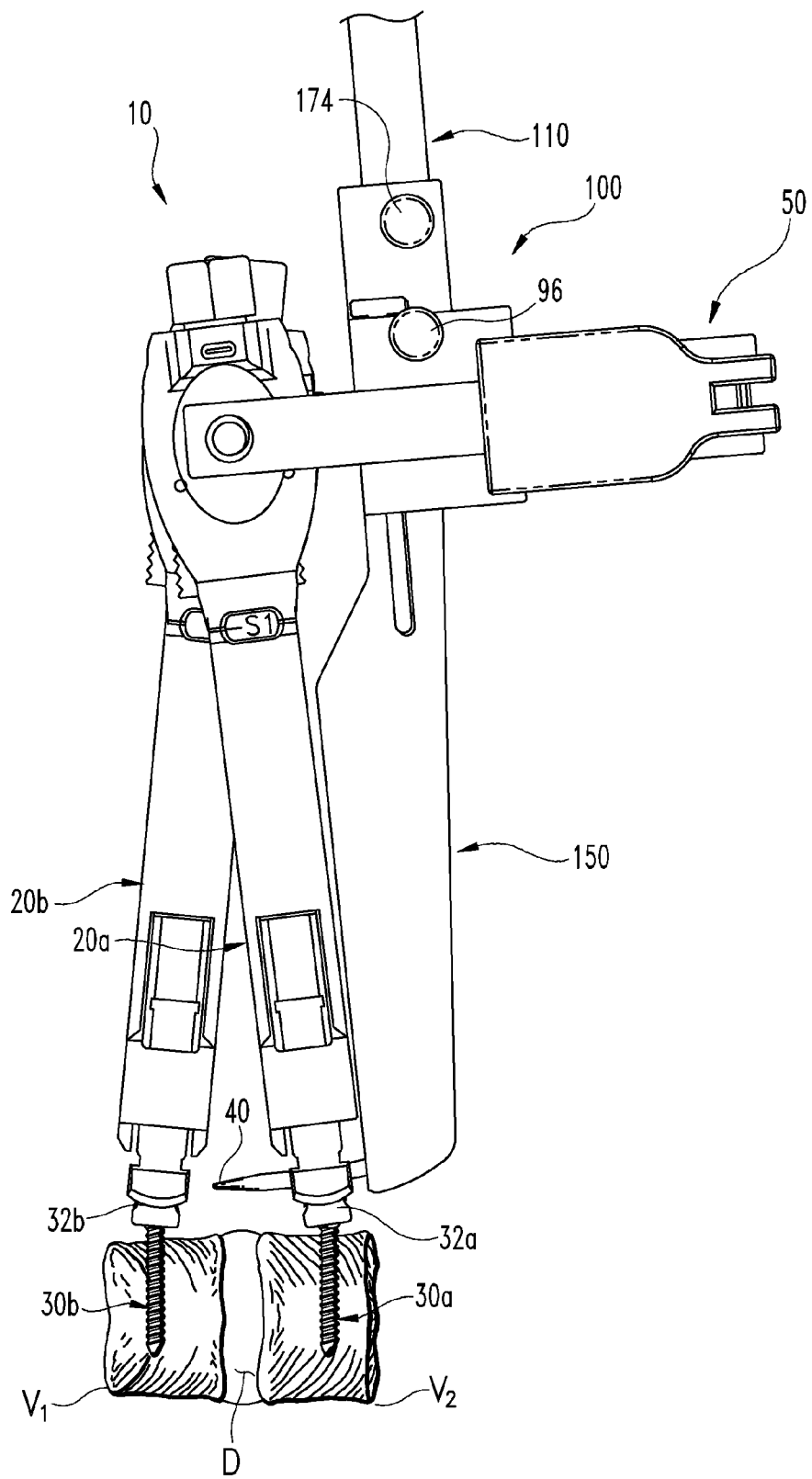

In FIG. 17, engaging member 110 has been moved further distally relative to elongated housing 150 such that the leading end 40a of connecting element 40 is positioned adjacent to proximal receiving portion 32b of anchor 30b. In addition, elongated housing 150 has also been moved distally relative to mounting assembly 50 such that the angle of connecting element 40 relative to vertebrae $V_1, V_2$ is reduced. Amongst other things, this change in angle prevents interference of the leading end 40a of connecting element 40 with anchor 30b or surrounding patient anatomy, and allows leading end 40a of connecting element 40 to advance toward proximal receiving portion 32b. In other forms however, it is contemplated that positioning of 40a leading end of connecting element 40 adjacent to proximal receiving portion 32b would not require distal movement of elongated housing 150 relative to mounting assembly 50. In addition, while not previously discussed, it should be appreciated that distal motion of engaging member 110 and elongated housing 150 may be performed simultaneously or in a step-wise manner as appropriate. Once an appropriate angle of connecting element 40 has been obtained, locking member 96 may be tightened against elongated housing 150 again to fix the axial positioning of elongated housing 150 relative to mounting assembly 50.

Figure 18:
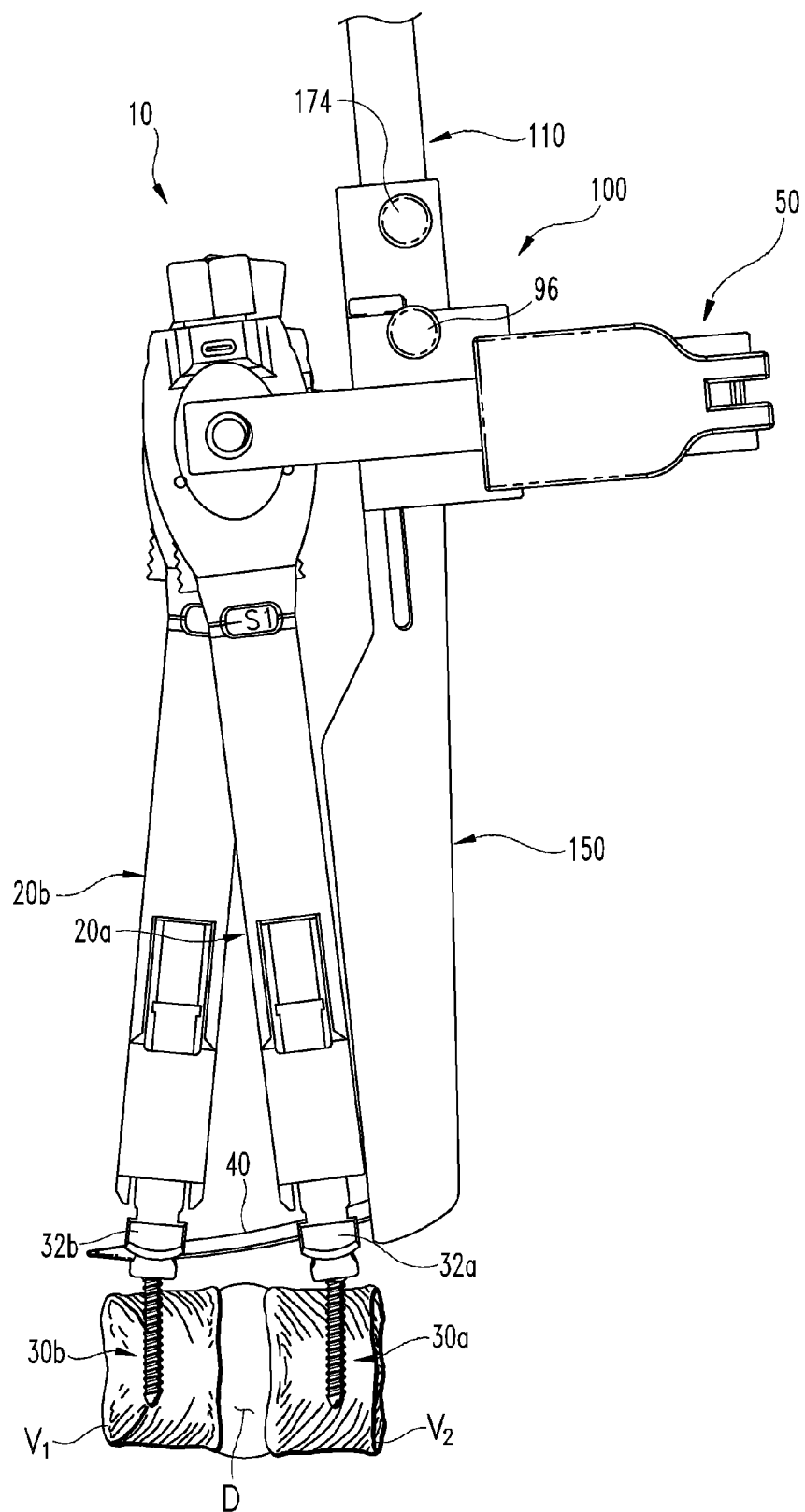

Distal movement of engaging member 110 relative to elongated housing 150 may be continued until connecting element 40 extends through distal slots in inner members 24a, 24b of anchor extenders 20a, 20b above anchors 30a, 30b as illustrated in FIG. 18. In this arrangement, coupling portion 122 of engaging member 110 may bear against distal surface 162 such that it is pivoted away from longitudinal axis L and extends substantially perpendicular to elongated shaft portion 112. Similarly, as illustrated in FIG. 18, the orientation of connecting element 40 has been rotated about ninety degrees relative to its orientation in internal chamber 160 in FIGS. 14 and 15. In addition, connecting element 40 is also generally aligned so that it can be reduced into proximal receiving portions 32a, 32b of anchors 30a, 30b.

Figure 19:
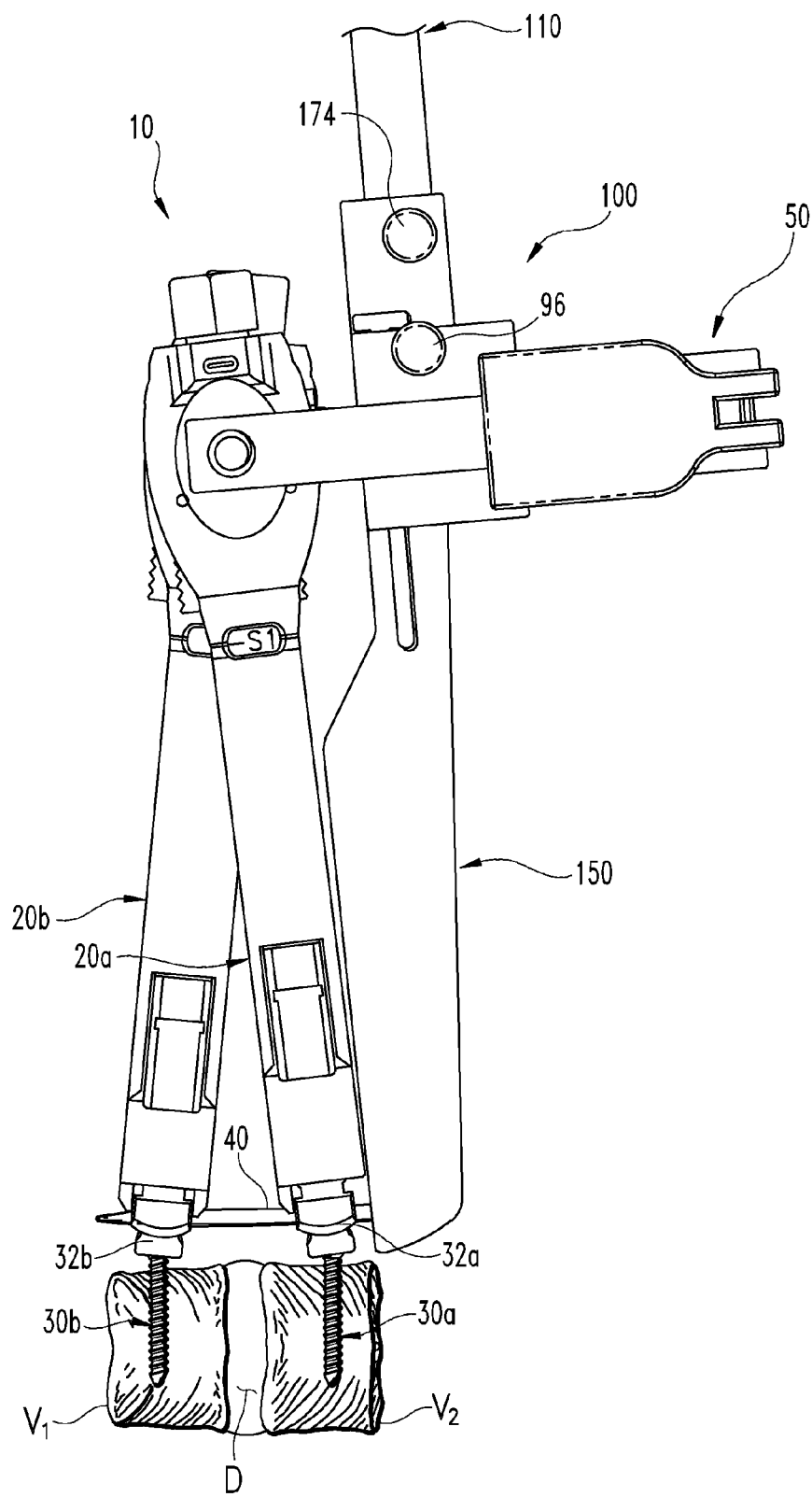

Once connecting element 40 is arranged in this manner, outer member assemblies 22a, 22b can be moved distally relative to inner members 24a, 24b to engage with connecting element 40 and reduce it into proximal receiving portions 32a, 32b of anchors 30a, 30b as illustrated in FIG. 19. Since mounting assembly 50 is engaged with outer member assemblies 22a, 22b, it also moves distally as outer member assemblies 22a, 22b are moved distally. Similarly, since the axial position of elongated housing 150 is fixed relative to mounting assembly 50 by locking member 96, it is also moved distally as connecting element 40 is reduced into proximal receiving portions 32a, 32b by distal movement of outer member assemblies 22a, 22b. While not previously discussed, it should be appreciated that the axial positioning of engaging member 110 relative to mounting assembly 150 may be locked or unlocked as connecting element 40 is reduced into proximal receiving portions 32a, 32b with outer member assemblies 22a, 22b. However, if the axial positioning of engaging member 110 is locked relative to mounting assembly 50, it should be appreciated that engaging member 110 should be advanced to its distal most position to allow connecting element 40 to be properly reduced into proximal receiving portions 32a, 32b. In other non-illustrated configurations, it is contemplated that alternatively configured anchor extenders may be used in system 10. In one or more forms of these configurations, one or more instruments may be inserted through the anchor extender to reduce connecting element 40 into proximal receiving portions 32a, 32b in lieu of outer member assemblies 22a, 22b.

Following reduction of connecting element 40 in proximal receiving portions 32a, 32b of anchors 30a, 30b, a locking member, such as a set screw for example, may be introduced through each of anchor extenders 20a, 20b and engaged with proximal receiving portions 32a, 32b of anchors 30a, 30b to secure connecting element 40 relative to anchors 30a, 30b. An instrument, such as a screw-driver for example, may then be introduced through passage 172 of elongated housing 150 into engagement with locking member 146 and rotated as appropriate to disengage locking member 146 from connecting element 40 in internal receptacle 142 of coupling portion 122. Mounting assembly 50 may then be pivoted proximally relative to anchor extenders 20a, 20b which will in turn move distal end portion 154 of elongated housing 150 away from anchor extender 20a. Similarly, connecting element 40 becomes disengaged from coupling portion 122 as mounting assembly 50 is pivoted in this manner, and inserter instrument 100 may be subsequently removed from the surgical site. Alternatively, it is also contemplated that mounting assembly 50 may be disengaged from proximal end portions 26a, 26b of anchor extenders 20a, 20b to allow a user to disengage coupling portion 122 from connecting element 40 and then remove mounting assembly 50 and inserter instrument 100 from the surgical site.

Figure 20:
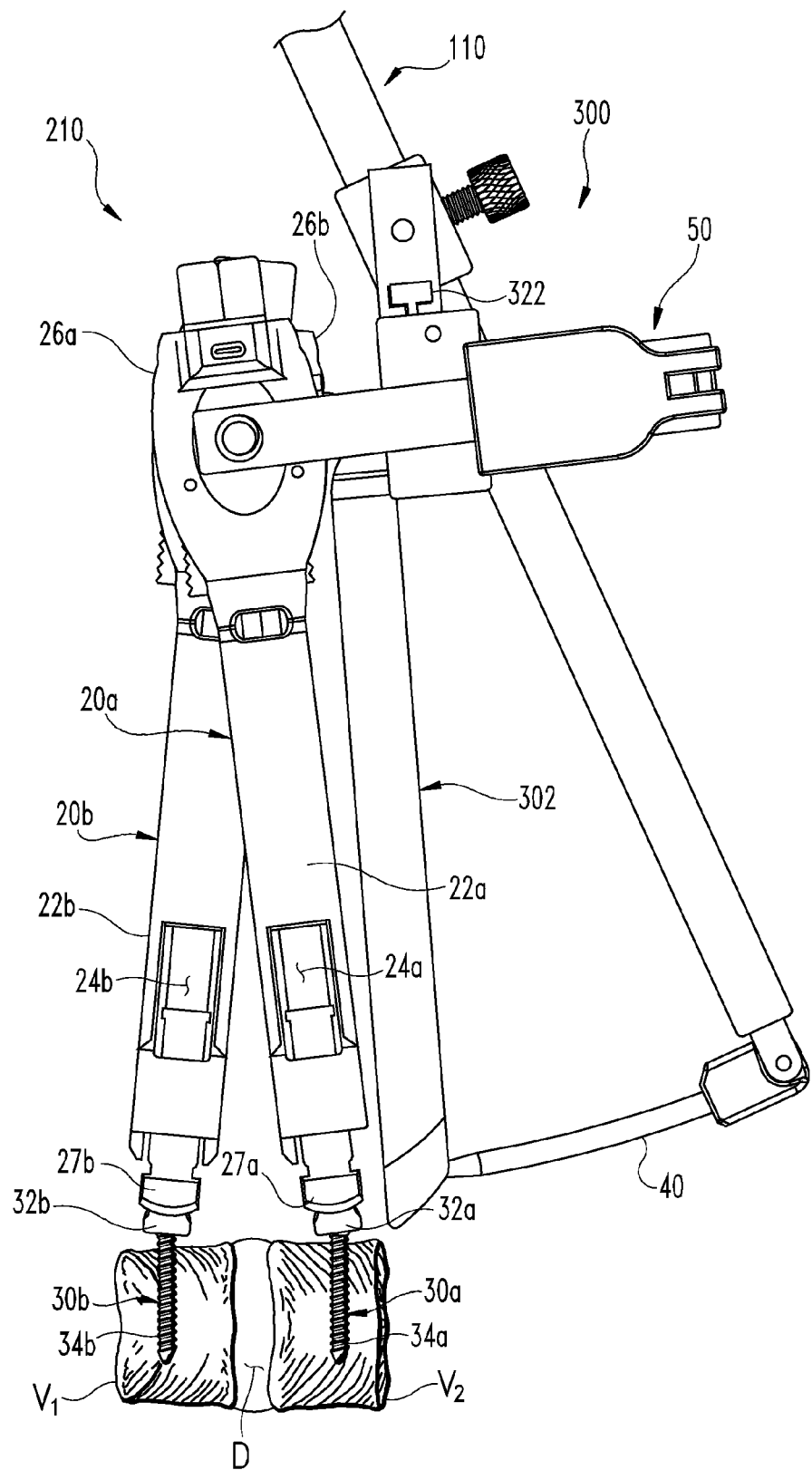
FIG. 20 is a perspective view of an alternative embodiment system for positioning a connecting element in a patient in minimally invasive surgical procedures.
Figure 21:
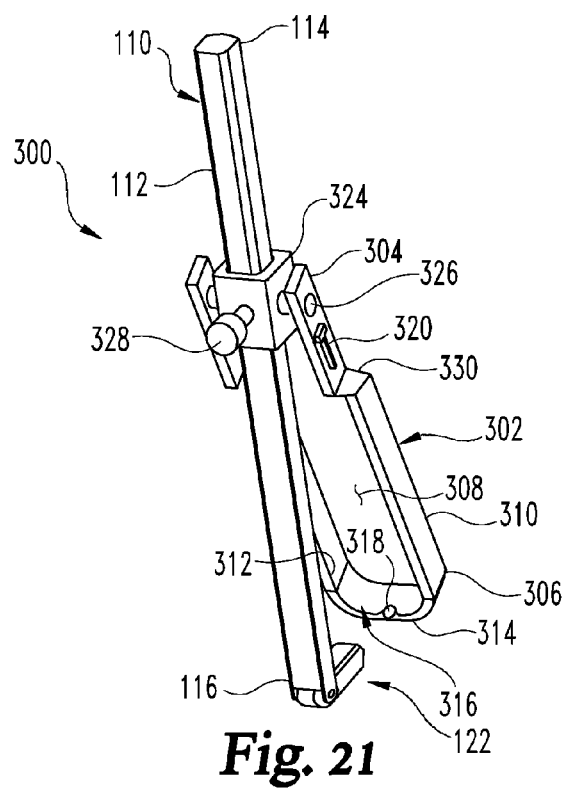
FIG. 21 is a perspective view of the inserter instrument illustrated in FIG. 20.
Figure 22:
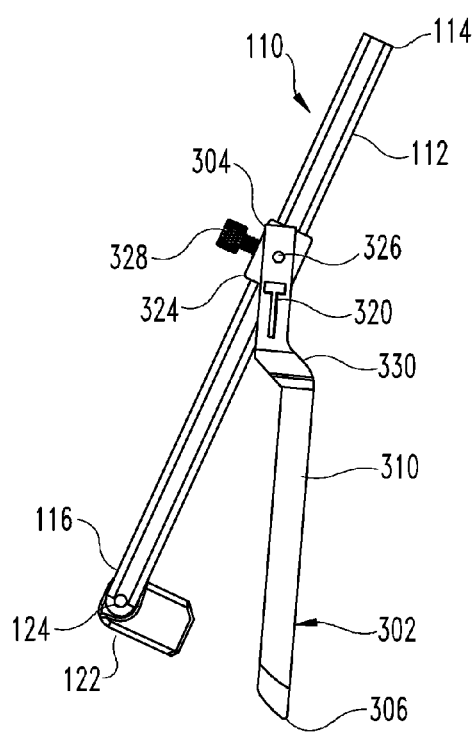
FIG. 22 is a plan view of the inserter instrument illustrated in FIG. 20.

Referring now generally to FIG. 20, where like numerals refer to like features of system 10 previously described, an alternative embodiment minimally invasive surgical system 210 is illustrated. System 210 is substantially similar to system 10 and is also configured to position connecting element 40 adjacent to proximal receiving portions 32a, 32b of anchors 30a, 30b. However, in contrast to system 10, system 210 utilizes inserter instrument 300 in lieu of inserter instrument 100. As illustrated in FIGS. 21 and 22, inserter instrument 300 includes engaging member 110 which is axially movable and pivotally mounted relative to an elongated body 302. Elongated body 302 is generally positionable in mounting assembly 50 and alongside and adjacent to anchor extender 20a as illustrated in FIG. 20. Elongated body 302 also extends between a proximal end portion 304 and a distal end portion 306 and includes a hollow interior or passage 308. Interior 308 has a generally U-shaped configuration and is surrounded by a pair of opposite side members 310, 312. At distal end portion 306, a distal member 314 extends between side members 310, 312 and provides a distal surface 316 that distally closes interior 308. Distal surface 316 includes an indentation 318 configured to engage with end 40a of connecting element 40. Distal surface 316 is also distally angled relative to side members 310, 312 in a direction extending away from engaging member 110. Furthermore, distal surface 316 and side members 310, 312 are generally configured to guide connecting element 40 adjacent to proximal receiving portions 32a, 32b as it is inserted with insertion instrument 300, further details of which will be provided below with respect to FIGS. 23-25.

Distal end portion 306 of elongated body 302 has a rounded or arcuate configuration to eliminate interference between elongated body 302 and adjacent tissue and/or muscle as elongated body 302 is positioned at a surgical site. Moreover, as discussed above with respect to elongated housing 150, it is contemplated that elongated body 302 may be positioned in the same incision through which anchor extender 20a extends into engagement with anchor 30a. Elongated body 302 also includes an offset portion 330 positioned between proximal end portion 304 and distal end portion 306 such that proximal and distal end portions 304, 306 are offset from one another. In addition, oppositely positioned T-shaped projections 320, 322 are positioned on side members 310, 312, respectively, proximally of offset portion 330. Projections 320, 322 are configured to engage and cooperate with slots 94a, 94b of channel 90 of receiving portion 82 as discussed above with respect to projections 156, 158 of elongated housing 150 in order to limit distal movement of elongated body 302 relative to mounting assembly 50. In addition, locking member 96 of receiving portion 82 is also engageable against elongated body 302 in order to facilitate locking the axial position of elongated body 302 relative to receiving portion 82.

Proximal end portion 304 also includes a receiving member 324 positioned between and pivotally mounted to side members 310, 312 by pin 326. Receiving member 324 is generally configured to receive engaging member 110 which is axially movable relative to receiving member 324, although receiving member 324 also includes a locking member 328, such as a set screw for example, that is configured to engage against engaging member 110 to lock its axial positioning relative to receiving member 324. Thus, engaging member 110 is both axially slidable and pivotally movable relative to elongated body 302.

Figure 23:
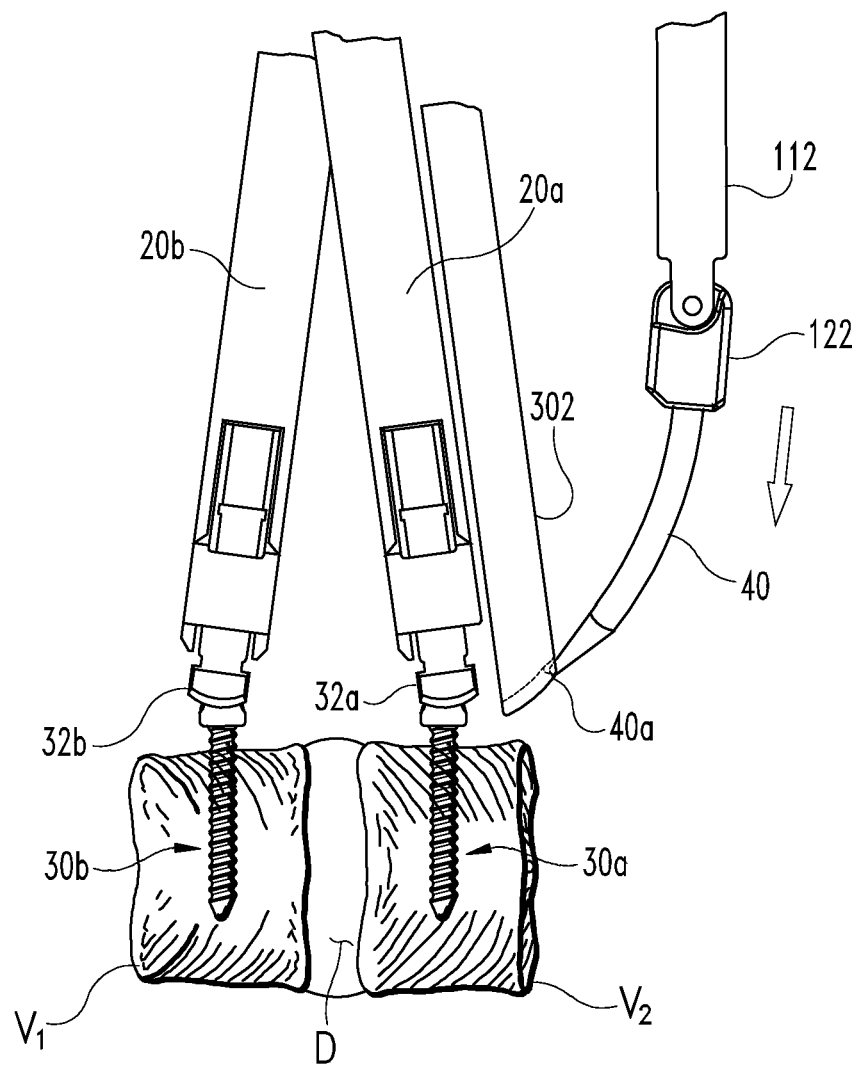
FIGS. 23-25 illustrate various steps of a minimally invasive surgical procedure for inserting a connecting element with the system illustrated in FIG. 20.

In use, engaging member 110 may be positioned in receiving member 324 and connecting element 40 may be securely engaged with coupling portion 122. End 40a of connecting element may then be positioned in indentation 318 of distal surface 316 as illustrated in FIG. 23. Inserter instrument 300 may then be positioned in receiving portion 82 of mounting assembly 50 such that elongated body 302 is positioned adjacent to and generally alongside anchor extender 20a. In addition, interior 308 of elongated body 302 is generally oriented toward anchor extender 20a and anchor 30a. As an alternative, it is contemplated that elongated body 302 may be positioned in receiving portion 82 of mounting assembly 50 followed by positioning of engaging member 110 with connecting element 40 coupled therewith through receiving member 324. However, regardless of order, it should be appreciated that in the configuration illustrated in FIG. 23, indentation 318 will provisionally retain end 40a of connecting element 40 until the angle of connecting element 40 relative to elongated body 302 changes enough to dislodge end 40a from indentation 318. For example, as engaging member 110 is moved distally as indicated by the corresponding directional arrow in FIG. 23, end 40a of connecting element 40 is pivoted proximally away from the bottom of indentation 318 while coupling portion 122 is pivoted relative to elongated shaft portion 112 of engaging member 100.

Figure 24:
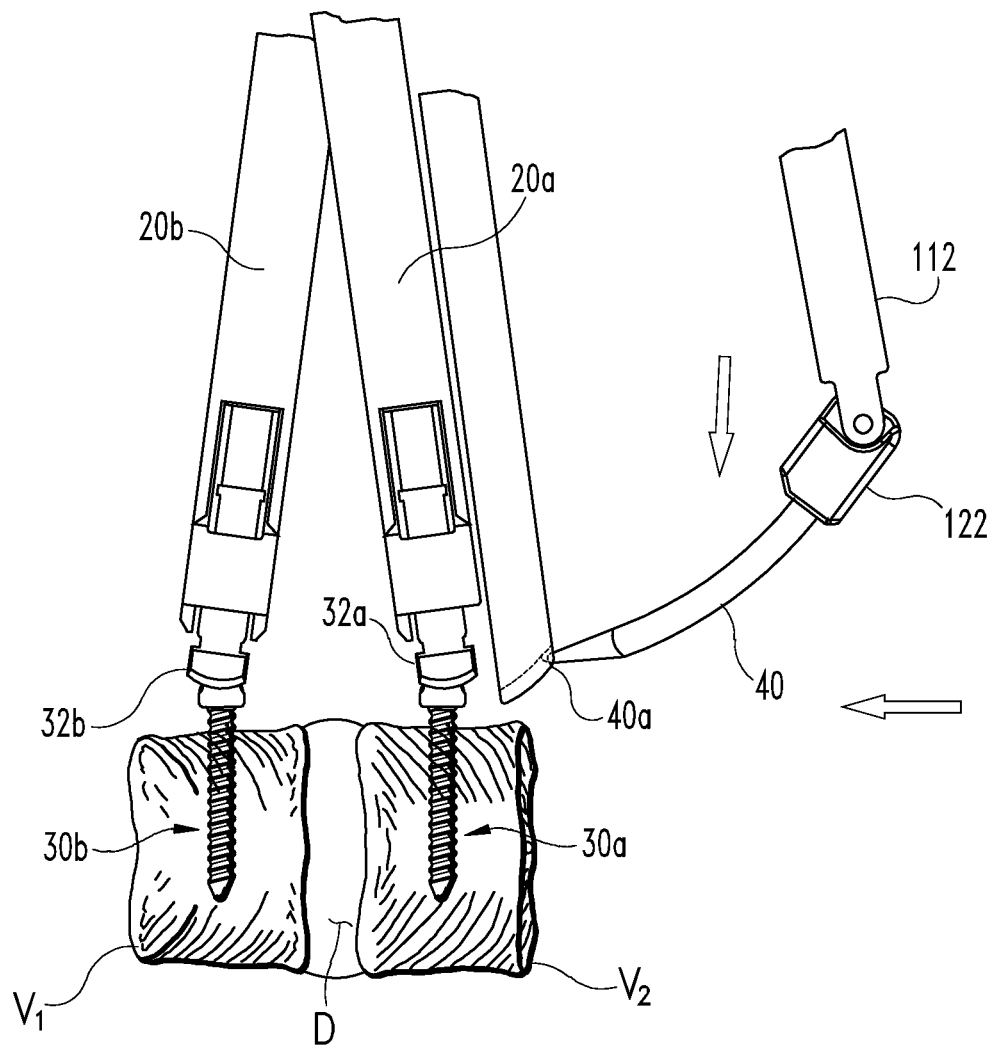
Figure 25:
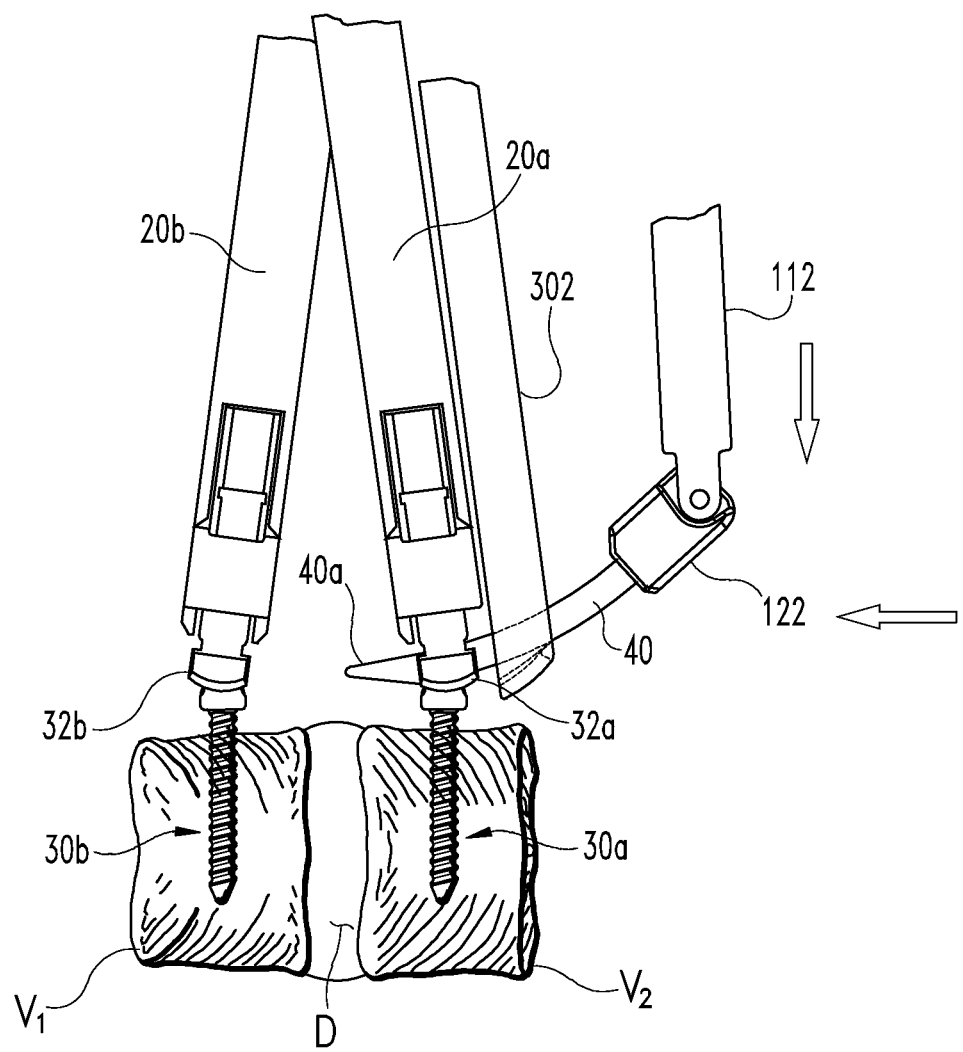

Upon further distal movement of engaging member 110, end 40a is pivoted out of indentation 318 such that, upon pivotal rotation of engaging member 110 toward elongated body 302 as indicated by the corresponding directional arrow in FIG. 24, connecting element 40 may pass through interior 308 of elongated body 302 toward anchor extender 20a and anchor 30a. Indeed, as illustrated in FIG. 25, end 40a of connecting element 40 is positioned between anchors 30a and 30b. As engaging member 110 is further moved distally and pivoted toward elongated body 302 from the configuration illustrated in FIG. 25, end 40a of connecting element will be directed toward anchor 30b such that connecting element 40 is aligned for reduction into proximal receiving portions 32a, 32b of anchors 30a, 30b. Thus, inserter instrument 300 can be used to insert connecting member 40 through various cooperating phases of distal and pivotal movement of engaging member 110. As one alternative, it is contemplated that one or more of the distal and pivotal movements of engaging member 110 could be performed simultaneously. As another alternative, it is also contemplated that most of the distal movement of engaging member 110 could be performed first such that connecting member 40 is generally aligned with vertebrae $V_1$, $V_2$ before engaging member 110 is pivoted. Engaging member 110 could then be pivoted in order to laterally advance connecting element 40 adjacent to proximal receiving portions 32a, 32b of anchors 30a, 30b.

When connecting element 40 is aligned with anchors 30a, 30b and prepared for reduction, elongated shaft portion 112 of engaging member 110 will be positioned adjacent to elongated body 302 and coupling portion 122 will be positioned in interior 308. Accordingly, once connecting element 40 is reduced and secured to anchors 30a, 30b as discussed above with respect to system 10, an instrument such as a screwdriver can be positioned between side members 310, 312 at offset portion 330 to engage and rotate locking member 146 as appropriate in order to disengage locking member 146 from contact with connecting element 40 so that connecting element 40 can be removed from internal receptacle 146 of coupling portion 122. Engaging member 110 can then be rotated away from connecting element 40 and retracted proximally from the surgical site. Similarly, elongated body 302 and the remaining instrumentation may also be removed from the surgical site.

In one embodiment, systems for positioning a connecting element adjacent the spinal column in minimally invasive surgical procedures include one or more extenders removably engaged to one or more anchors engaged to a bony segment. The anchor extenders provide a reference to the respective anchor locations within the patient even when the anchor is obstructed by skin and/or tissue of the patient. Similarly, the anchor extenders are sized such that a portion thereof extends above the skin of a patient when they are engaged to the bone anchors. In one form, it is contemplated that separate incisions may be made for using and positioning each anchor and anchor extender. An inserter instrument can be removably mounted to the one or more anchor extenders and is operable to position a stabilization element relative to the anchors for engagement to the anchors to stabilize the bony segments to which the anchors are engaged. In one form, the inserter instrument may be positioned alongside an anchor extender and in the same incision in which the respective anchor extender is positioned. Still, it should be appreciated that alternative forms, aspects, configurations, arrangements and methods are contemplated with respect to the subject matter disclosed and described herein.

Alternative configurations of the systems described herein are also contemplated. For example, in one or more forms the systems described herein can be configured to insert a connecting element that extends across and is engaged to anchors positioned at three or more vertebral levels or to three or more bony portions or segments. In addition, use of the system described herein for stabilization of bones, bony structures or other anatomical features besides vertebral stabilization are contemplated. Furthermore, the systems and instrumentation described herein may also be used in surgical procedures involving animals, or in demonstrations for training, education, marketing, sales and/or advertising purposes. In addition, the systems and instrumentation described herein may be also used on or in connection with a non-living subject such as a cadaver, training aid or model, or in connection with testing of surgical systems, surgical procedures, orthopedic devices and/or apparatus.

Any theory, mechanism of operation, proof, or finding stated herein is meant to further enhance understanding of the present application and is not intended to make the present application in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the application, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the application as defined herein or by any of the following claims are desired to be protected.

What is claimed is:

1. A system for minimally invasive surgery, comprising:
   at least one bone anchor including a distal bone engaging portion and a proximal receiving portion;
   at least one extender including a body extending between a proximal end portion and a distal end portion configured to releasably engage with said at least one bone anchor;
   a mounting assembly releasably engageable with said proximal end of said at least one extender, said mounting assembly including a receiving portion;
   an inserter instrument including a guide member and a connecting element engaging member axially movable relative to said guide member, said connecting element engaging member including an elongated shaft portion and a coupling portion pivotally coupled with said elongated shaft portion, said coupling portion including a receptacle structured to releasably receive an end portion of said connecting element; and
   wherein said inserter instrument is positionable in said receiving portion of said mounting assembly with said guide member positioned adjacent to said at least one extender such that said guide member guides a connecting element toward said proximal receiving portion of said at least one bone anchor as said connecting element engaging member is moved distally.

2. The system of claim 1, wherein said receptacle includes an internal configuration and said end portion of said connecting element includes an external configuration that corresponds to said internal configuration of said receptacle.

3. The system of claim 2, wherein said external configuration of said end portion of said connecting element is conical.

4. The system of claim 1, wherein said coupling portion includes a transverse bore communicating with said receptacle, said transverse bore including a locking member configured to releasably lock said end portion of said connecting element in said receptacle.

5. The system of claim 1, wherein said at least one bone anchor includes a pair of bone anchors and said at least one extender includes a pair of extenders.

6. The system of claim 5, wherein said mounting assembly includes a pair of oppositely positioned engaging arms, each of said engaging arms including a projection structured to engage with a receptacle in the proximal end portions of each one of said pair of extenders.

7. The system of claim 1, wherein said mounting assembly includes a first engaging arm positioned on a first side of said receiving portion and a second engaging arm positioned on an opposite, second side of said receiving portion.

8. The system of claim 7, wherein said second engaging arm is pivotally movable relative to said first engaging arm and said receiving portion and said mounting assembly includes a cam member configured to move said second engaging arm between a first position in which said mounting assembly is disengaged from said at least one extender and a second position in which said mounting assembly is engaged with said at least one extender.

9. The system of claim 1, wherein said receiving portion is defined by a U-shaped channel, said channel including a pair of slots configured to receiving corresponding projections on said inserter instrument, said slots and said projections cooperating to limit distal positioning of said inserter instrument relative to said receiving portion.

10. A system for minimally invasive surgery, comprising:
    at least one bone anchor including a distal bone engaging portion and a proximal receiving portion;
    at least one extender including a body extending between a proximal end portion and a distal end portion configured to releasably engage with said at least one bone anchor; and
    an inserter instrument positionable adjacent to and alongside said at least one extender, said inserter instrument including:
      an elongated housing extending along a longitudinal axis between a proximal end and a distal end, said elongated housing including an internal chamber terminating distally at a distal surface and including a lateral opening extending through a side portion of said elongated housing, said distal surface including a groove formed therein, said groove extending obliquely to said longitudinal axis;
      a connecting element engaging member communicating with said internal chamber and including a distal end portion configured to engage with a connecting element; and wherein said connecting element engaging member is operable to move said connecting element distally into engagement with said distal surface and said distal surface is configured to change an orientation of said connecting element and guide said connecting element through said lateral opening toward said proximal receiving portion of said at least one bone anchor as said connecting element engaging member is moved distally.

11. The system of claim 10, wherein said elongated housing further includes a first elongated passage communicating with said internal chamber and receiving at least a portion of said connecting element engaging member, said first elongated passage being off-centered relative to said internal chamber.

12. The system of claim 11, wherein said elongated housing includes a second elongated passage spaced apart from and extending substantially parallel to said first elongated passage, said second elongated passage communicating with said internal chamber.

13. The system of claim 10, wherein said elongated housing includes a locking member configured to releasably lock axial positioning of said connecting element engaging member relative to said elongated housing.

14. The system of claim 10, wherein said distal surface extends transversely to said longitudinal axis.

* * * * *